US011622923B2

(12) United States Patent
Cassin et al.

(10) Patent No.: US 11,622,923 B2
(45) Date of Patent: Apr. 11, 2023

(54) EMULSIONS STABILISED BY AMPHIPHILIC COMPOSITE PARTICLES

(71) Applicant: L'OREAL, Paris (FR)

(72) Inventors: Guillaume Cassin, L'Hay les Roses (FR); Bruno Biatry, Vincennes (FR); Romuald Sanchez, Chevilly-Larue (FR)

(73) Assignee: L'OREAL, Paris (FR)

(*) Notice: Subject to any disclaimer, the term of this patent is extended or adjusted under 35 U.S.C. 154(b) by 180 days.

(21) Appl. No.: 15/536,830

(22) PCT Filed: Dec. 17, 2015

(86) PCT No.: PCT/FR2015/053608
§ 371 (c)(1),
(2) Date: Jun. 16, 2017

(87) PCT Pub. No.: WO2016/097641
PCT Pub. Date: Jun. 23, 2016

(65) Prior Publication Data
US 2017/0360661 A1 Dec. 21, 2017

(30) Foreign Application Priority Data

Dec. 17, 2014 (FR) ...................................... 1462576

(51) Int. Cl.
*A61K 8/11* (2006.01)
*A61K 8/25* (2006.01)
*A61K 8/73* (2006.01)
*A61Q 19/00* (2006.01)
*A61K 8/81* (2006.01)
*A61K 8/891* (2006.01)
*A61K 8/06* (2006.01)
*A61K 8/29* (2006.01)
*A61K 8/02* (2006.01)
*A61K 8/19* (2006.01)

(52) U.S. Cl.
CPC .............. *A61K 8/11* (2013.01); *A61K 8/0241* (2013.01); *A61K 8/062* (2013.01); *A61K 8/19* (2013.01); *A61K 8/25* (2013.01); *A61K 8/29* (2013.01); *A61K 8/731* (2013.01); *A61K 8/8152* (2013.01); *A61K 8/891* (2013.01); *A61Q 19/00* (2013.01); *A61K 2800/10* (2013.01); *A61K 2800/33* (2013.01); *A61K 2800/412* (2013.01); *A61K 2800/52* (2013.01); *A61K 2800/612* (2013.01); *A61K 2800/614* (2013.01); *A61K 2800/623* (2013.01); *A61K 2800/624* (2013.01); *A61K 2800/651* (2013.01); *A61K 2800/652* (2013.01); *A61K 2800/654* (2013.01)

(58) Field of Classification Search
CPC .... A61K 8/11; A61K 8/062; A61K 2800/652; A61K 2800/412; A61K 2800/654; A61K 8/19; A61K 8/06; A61K 8/8152; A61K 8/731; A61K 2800/624; A61K 2800/52; A61K 2800/614; A61K 2800/612; A61K 2800/10; A61Q 19/00
See application file for complete search history.

(56) References Cited

U.S. PATENT DOCUMENTS

| 6,511,655 | B1* | 1/2003 | Muller | A61K 8/046 424/401 |
| 2002/0192260 | A1* | 12/2002 | Victor | A61K 8/8147 424/419 |
| 2003/0091824 | A1* | 5/2003 | Kim | C08L 51/10 428/404 |
| 2004/0191281 | A1* | 9/2004 | Becher | A61K 9/1611 424/401 |
| 2005/0112074 | A1 | 5/2005 | Arai et al. | |
| 2006/0153889 | A1* | 7/2006 | Friel | A61K 8/345 424/401 |
| 2011/0110994 | A1 | 5/2011 | Inokuchi et al. | |
| 2013/0287826 | A1 | 10/2013 | Cao et al. | |
| 2013/0309285 | A1* | 11/2013 | Matsufuji | C09B 67/0063 424/401 |
| 2016/0030304 | A1 | 2/2016 | Nagamatsu et al. | |

FOREIGN PATENT DOCUMENTS

| CN | 1599591 A | | 3/2005 |
| CN | 102061092 A | | 5/2011 |
| CN | 103210030 A | | 7/2013 |
| EP | 2325261 A1 | | 5/2011 |
| EP | 2670378 | * | 8/2017 |
| JP | 2-49717 A | | 2/1990 |
| JP | 7-31864 A | | 2/1995 |
| JP | 8-59435 A | | 3/1996 |

(Continued)

OTHER PUBLICATIONS

"Particle", Merriam-Webster, <https://www.merriam-webster.com/dictionary/particle>, published Jan. 21, 2013, p. 1.*
Shakerizadeh-shirazi et al. (Analytical Methods, 2013; 5. 891).*
International Search Report dated Feb. 24, 2016, in PCT/FR2015/053608, filed Dec. 17, 2015.
Combined Chinese Office Action and Search Report dated Feb. 3, 2020, in Patent Application No. 201580076371.0, 10 pages (with English Translation of Category of Cited Documents).
Office Action dated Sep. 2, 2019 in Japanese Patent Application No. 2017-532884, 18 pages (with English translation).

Primary Examiner — Shirley V Gembeh
(74) Attorney, Agent, or Firm — Womble Bond Dickinson (US) LLP

(57) ABSTRACT

The present invention relates to an emulsion not containing any emulsifying surfactant, in particular to an oil-in-water emulsion not containing any emulsifying surfactant, characterized in that it comprises, especially in a physiologically acceptable medium, at least composite particles comprising a core comprising at least organic or inorganic particles A; said core being covered at the surface, continuously or discontinuously, with an envelope comprising at least organic or inorganic particles B; said particles A and B having different polarities.

19 Claims, No Drawings

(56) References Cited

FOREIGN PATENT DOCUMENTS

| | | |
|---|---|---|
| JP | 2005-220314 A | 8/2005 |
| JP | 2006-219437 A | 8/2006 |
| JP | 2008-7536 A | 1/2008 |
| JP | 2010-265198 A | 11/2010 |
| JP | 2011-83753 A | 4/2011 |
| JP | 2011-102354 A | 5/2011 |
| WO | 03/047541 A1 | 6/2003 |
| WO | 2012/069291 A1 | 5/2012 |
| WO | WO 2012/104161 * | 8/2012 |
| WO | WO 2014/009097 A1 | 1/2014 |
| WO | 2014/161722 A1 | 10/2014 |
| WO | 2014/184224 A1 | 11/2014 |

* cited by examiner

EMULSIONS STABILISED BY AMPHIPHILIC COMPOSITE PARTICLES

CROSS-REFERENCE TO RELATED APPLICATIONS

This application is the National Stage of PCT/FR2015/053608, filed Dec. 17, 2015, the disclosure of which is incorporated herein by reference in its entirety. PCT/FR2015/053608 claims priority to French Application No. 1462576, filed Dec. 17, 2014, the disclosure of which is incorporated herein by reference in its entirety.

BACKGROUND

The present invention relates to an emulsion not containing any emulsifying surfactant, comprising, especially in a physiologically acceptable medium, at least composite particles comprising a core comprising at least organic or inorganic particles A; said core being covered at the surface, continuously or discontinuously, with an envelope comprising at least organic or inorganic particles B; said particles A and B having different polarities.

The present invention also relates to the use of the composite particles as defined previously as emulsion stabilizer, in particular for an emulsion not containing any emulsifying surfactant, and more particularly for an oil-in-water emulsion not containing any emulsifying surfactant.

The present invention also relates to a cosmetic process for treating a keratin material, which consists in applying to the keratin material an emulsion as defined previously.

In the cosmetics field, it is common practice to formulate emulsions such as oil-in-water (O/E) emulsions. These emulsions are most particularly advantageous for their sensory properties. However, these cosmetic emulsions are, generally, stabilized with surfactants that can be a kerb in certain applications. Specifically, surfactants, in particular as emulsifiers, may affect the cosmeticity of products and the powdery nature of the deposit, which is greatly appreciated by consumers. These surfactants may also cause certain negative effects, such as a sticky, slippery or soapy effect.

Liquid/liquid emulsions, in particular oil-in-water (O/E) emulsions, are by nature unstable, and undergo intense stress due to evaporation of the volatile phase after application. This stress leads to coalescence of the drops of the dispersed phase and the phenomenon is all the more pronounced when the interface is fluid and non-cohesive, as is the case for conventional surfactants. This instability does not make it possible to control the state of the residual film after application and may lead to degradation of its optical properties (gloss, mattness, absorption) and/or its sensory properties.

Moreover, on account of the nature of the residual film, containing a large amount of surfactant or of amphiphilic polymer, it is difficult to maintain its properties over time in the face of stressing factors such as sweat, sebum or seawater in the case of photoprotection products.

A solution to the problem may be provided by using amphiphilic solid particles that are capable of being adsorbed at the water/oil interface and of stabilizing the emulsion without adding surfactant. It is particularly advantageous to provide surfactant-free emulsions in order to limit the problems of harmlessness and sensitization, and moreover to reduce the environmental impact. These systems, initially described by Ramsden [Proc. Roy. Soc., 72, 156 (1903)] and Pickering [J. Chem. Soc., 91, 2001 (1907)] have since been the subject of numerous studies [Colloidal Particles at Liquid Interface, Ed. B. P. Binks and T. S. Horozov, Cambridge University Press 2006].

Several examples of particles have been described, such as modified nanosilicas [Binks B. P., Langmuir, 16, 8622, (2000)], morphologies of "Janus" type [Perro S., Coll. Surf. A, 332, 57, (2009)], or "bowl" type [Nonomura Y., Langmuir, 27, 4557, (2011)], functionalized clays [Mejia A. F., Soft Matter, 8, 10245, (2012)], modified starches [Tan Y., Carbohyd. Polym., 88, 1358, (2012)], microsphere/nanosphere composites [Fleming M., Chem. Mater., 13, 2210, (2001)]. These technical solutions however have the drawback of being complex to implement and do not allow control/modulation of the degree of amphiphilicity of the particle. Moreover, these particles do not have intrinsic properties (optical or sensory) that are advantageous for the cosmetic field.

Several solutions have been proposed in the cosmetic field for stabilizing emulsions, especially O/E emulsions, with the aid of solid particles. Patent applications US 2011/0 178 207 and US 2007/0 209 552 have proposed using submicronic fumed silica, which has undergone a surface treatment. Patent FR 2 995 784 describes the use of magnesium silicates for fragrancing compositions and also the use of modified silica or clays for hair compositions to be shaken before use. Also in patent FR 2 991 180, submicronic fumed silica has been proposed in the patent for stabilizing retinoid emulsions. Micronized pigments less than 200 nm in size have also been proposed in patent EP 969 802. Patent application WO 2012/082 065 mentions using chemically or thermally modified starch microparticles for preparing emulsions.

Solid treatment solutions not involving a covalent bond, as seen above, but using the adsorption of a cationic surfactant, have been described in patents EP 2 149 361 and EP 1 958 687, and also complexation with a cellulose derivative, in patent application WO 09/112 836.

In general, the amphiphilic particles obtained via the adsorption techniques have the following drawbacks:
  the molecules adsorbed have a tendency to become detached from the surface of the amphiphilic particles depending on the environmental conditions around the particles, thus leading to loss over time of the amphiphilic properties of said particles;
  it is difficult to control the degree of surface area modified on account of the use of small-sized adsorbed molecules;
  it is difficult to measure the degree of surface area modified without special equipment;
  the processes for preparing amphiphilic particles are complex to implement. For example, a purification step is necessary to remove the non-adsorbed molecules.

Furthermore, in certain cases, a spraying step and/or a milling step may be necessary to prepare the amphiphilic particles (for example as indicated in patent application JP-A-2011-83753). It is difficult to control the amphiphilic properties by adjusting this spraying step and/or this milling step.

Moreover, as a type of surface modification technique, it is known to attach small molecules to the particles via covalent bonding. For example, hydrophilic silica particles may be treated with a silane coupling agent to form a hydrophobic film that is attached via covalent bonding to the surface of the silica particles. The treated surface of the silica particles may (Hyomen, Vol. 41, No. 6, p. 28-34 (2003)). In this case also, controlling the amphiphilic properties of the particles thus obtained is difficult. Furthermore, it is often necessary to make use of a purification step in order to remove the unreacted reagents. It is difficult to control the degree of surface area modified on account of the use of small-sized adsorbed molecules.

Patent EP 2 643 397 describes the use of composite particles, of core/shell structure, obtained by polymerization of an acrylic monomer at the surface of particles with a high refractive index. These particles have soft-focus optical properties, but there amphiphilic properties at the water/oil interfaces and the possibility of stabilizing emulsions was not described or suggested.

The need thus remains to find novel systems for stabilizing emulsions, which are easy to prepare and which make it possible to make stable emulsions that are friendly to keratin materials such as the skin and that are, in this respect, free of emulsifying surfactants, without the drawbacks mentioned previously, and which can give good optical properties (gloss, mattness, absorption) and/or good sensory properties.

SUMMARY OF THE INVENTION

Surprisingly, the Applicant has discovered that this objective can be achieved by using composite particles comprising a core comprising at least organic or inorganic particles A; said core being covered at the surface, continuously or discontinuously, with an envelope comprising at least organic or inorganic particles B; said particles A and B having different polarities.

In the course of their research, the inventors have discovered, surprisingly, composite particles with stabilizing properties for preparing surfactant-free emulsions, especially oil-in-water emulsions, also known as Pickering emulsions. These particles may be readily prepared via a chemical mechanofusion process which does not require a purification step and which makes it possible to control the amphiphilic properties of these composite particles.

According to the present invention, the shell particles are solidly attached to the surface of the particles constituting the core, to the point that it is difficult for the shell particles to become detached from the core particles, which allows, in a noteworthy manner, the composite particles to conserve their amphiphilic properties over time.

The present invention also relates to an emulsion not containing any emulsifying surfactant, and more particularly to an oil-in-water emulsion not containing any emulsifying surfactant, and comprising, especially in a physiologically acceptable medium, at least composite particles comprising a core comprising at least organic or inorganic particles A; said core being covered at the surface, continuously or discontinuously, with an envelope comprising at least organic or inorganic particles B; said particles A and B having different polarities.

Thus, one subject of the present invention is the use of said composite particles, as agent for stabilizing an emulsion, especially an emulsion not containing any emulsifying surfactant, and more particularly an oil-in-water emulsion not containing any emulsifying surfactant.

The present invention also relates to a cosmetic process for treating a keratin material, which consists in applying to the keratin material an emulsion as defined previously.

DESCRIPTION OF THE PREFERRED EMBODIMENTS

Definitions

For the purposes of the present invention, the term "emulsion" is intended to denote any composition comprising at least two phases that are liquid at room temperature (20-25° C.) and that are mutually immiscible; one of the two phases being dispersed in the other phase in the form of droplets so as to observe a mixture that is macroscopically homogeneous to the naked eye. In particular, the emulsions according to the invention are oil-in-water (O/E) emulsions, also known as direct emulsions.

For the purposes of the present invention, the term "physiologically acceptable medium" is intended to denote a medium that is suitable for the topical administration of a composition. A physiologically acceptable medium is a medium which has no unpleasant odor and/or appearance, and which is perfectly compatible with topical administration.

The term "keratin material" means the skin (bodily and facial skin), the lips and/or the integuments such as the nails.

"Not containing any emulsifying surfactant" means containing less than 1.00% by weight, preferably less than 0.50% by weight and even more preferably less than 0.10% by weight of emulsifying surfactant or even being totally free of emulsifying surfactant.

For the purposes of the present invention, the term "surfactant" means an amphiphilic molecule, i.e. a molecule that has two parts of different polarity, one generally being lipophilic (soluble or dispersible in an oily phase), and the other being hydrophilic (soluble or dispersible in water). Surfactants are characterized by their HLB (hydrophilic-lipophilic balance) value, the HLB being the ratio between the hydrophilic part and the lipophilic part in the molecule. The term "HLB" is well known to those skilled in the art and is described, for example, in "The HLB system. A time-saving guide to Emulsifier Selection" (published by ICI Americas Inc., 1984). For the emulsifying surfactants, the HLB generally ranges from 3 to 8 for the preparation of W/O emulsions and from 8 to 18 for the preparation of O/W emulsions. The HLB of the surfactant(s) used according to the invention may be determined via the Griffin method or the Davies method.

For the purposes of the invention, the term "cosmetic treatment" means any non-therapeutic fragrancing, hygiene, care, conditioning or makeup effect contributing toward improving the well-being and/or enhancing the beauty and/or modifying the appearance or odor of the keratin material onto which said composition is applied.

The presence of the composite particles in accordance with the present invention thus proves to be particularly advantageous for improving the stability of emulsions, in particular of oil-in-water emulsions (also known as direct emulsions), and also the stability of compositions comprising said emulsions.

In an equally surprising manner, it has been observed that the compositions comprising these emulsions have excellent optical properties such as a mattness or soft-focus effect.

It has also been demonstrated that the composite particles in accordance with the present invention are particularly effective for stabilizing said oil phase/aqueous phase interfaces, and for forming fine emulsions that are stable over time. The use of these composite particles thus reduces the need for surfactants, particularly surfactants of ionic and/or nonionic nature, and therefore improves the ease of use of compositions comprising the emulsion according to the invention.

Composite Particles

The composite particles in accordance with the invention comprise a core comprising at least organic or mineral particles A; said core being covered at the surface, continuously or discontinuously, with an envelope (or shell) comprising at least organic or mineral particles B; said particles A and B having different polarities.

The composite particles in accordance with the present invention are in particular amphiphilic.

For the purposes of the present invention, the term "amphiphilic composite particles" means that the composite particles have a hydrophilic part and a hydrophobic part; said hydrophilic and hydrophobic parts with different polarities allowing the composite particles to assemble at the interface between the water and the oil of a composition comprising oil and water.

The term "hydrophilic particles" means that all the particles are individually dispersed in the aqueous phase so as not to form an aggregate.

The term "hydrophobic particles" means that all the particles are individually dispersed in the oily phase so as not to form an aggregate.

The polarity of particles A and B constituting the composite particles of the invention may be defined by means of the scale $E_T(30)$, established by measuring the solvatochromic effect of a dye, such as 4-(2,4,6-triphenylpyridinium)-2,6-diphenylphenoxide (Reichardt's dye) on contact with the material. Reference may be made to the publication by Dimroth et al., [Justus Liebigs Annalen der Chemie, 661(1), 1-37, (1963)] for the principle. The values $E_T(30)$ were determined for different materials especially by Spange et al., [Langmuir, 15(6), 2103-2111, (1999)], [J. Phys. Chem. B, 104(27), 6417-6428, (2000)], ["Natural Fibre Reinforced Polymer Composites from Macro to Nanoscales", Old City Publishing, First Edition 2009, pages 47-72] and [Macromol. Rapid Commun. 21, 643-659 (2000)].

The parameter $E_T(30)$ (expressed in $kcal \cdot mol^{-1}$) ranges between 30.7 for tetramethylsilane and 63.1 for water.

If $\Delta E$ is defined as being the polarity difference, according to the scale $E_T(30)$, between material A (core) and material B (shell), it will be determined by the following equation:

$$\Delta E = E_T(30)A - E_T(30)B$$

In the context of the present application, particles A and B will be chosen such that the difference is greater than 2 and preferably greater than 5.

According to a particular form of the invention, the composite particles preferably have a mean size ranging from 0.1 to 100 µm, more preferentially from 0.5 to 15 µm and more particularly from 1 to 10 µm.

The term "mean particle size" means the mean diameter on 50% by volume of the particles (D[0,5]) obtained using a laser diffraction granulometer (e.g. Mastersizer 2000 from the company Malvern).

The composite particles in accordance with the invention may be non-spherical or non-spherical particles.

The term "spherical" is understood to mean that the particle has a sphericity index, i.e. the ratio between its largest diameter and its smallest diameter, of less than 1.2.

The term "non-spherical" refers to particles in three dimensions (length, width and thickness or height) for which the ratio of the longest dimension to the shortest dimension is greater than 1.2. The dimensions of the particles of the invention are evaluated by scanning electron microscopy and image analysis. They comprise particles of parallelepipedal shape (rectangular or square surface), discoid shape (circular surface) or ellipsoid shape (oval surface), characterized by three dimensions: a length, a width and a height. When the shape is circular, the length and the width are identical and correspond to the diameter of a disk, whereas the height corresponds to the thickness of the disk. When the surface is oval, the length and the width correspond respectively to the main axis and the minor axis of an ellipse and the height corresponds to the thickness of the elliptic disk formed by the platelet. When a parallelepiped is concerned, the length and the width can be of identical or different dimensions: when they are of the same dimension, the shape of the surface of the parallelepiped is square; in the contrary case, the shape is rectangular. As regards the height, it corresponds to the thickness of the parallelepiped.

According to a first variant of the invention, the composite particles in accordance with the invention comprise an envelope (or shell) that is continuous, i.e. it surrounds the entire surface of the core.

According to a second variant of the invention, the composite particles in accordance with the invention comprise an envelope (or shell) that is discontinuous, i.e. it discontinuously surrounds the surface of the core. Preferentially, from 10% to 90%, more particularly from 10% to 70% and even more particularly from 30% to 50% of the surface of the core is covered with the envelope.

According to a particular form of the invention, the particles A constituting the core of the composite particles are hydrophilic and the particles B constituting the envelope are hydrophobic.

According to another particular form of the invention, the particles A constituting the core of the composite particles are hydrophobic and the particles B constituting the envelope are hydrophilic.

The term "hydrophilic particles" means that all the particles are individually dispersed in the aqueous phase so as not to form an aggregate.

The term "hydrophobic particles" means that all the particles are individually dispersed in the oily phase so as not to form an aggregate.

Preferentially, the weight ratio of the core to the envelope of the composite particles of the invention ranges from 70/30 to 99.9/0.1, more preferentially from 80/20 to 99/1 and even more particularly from 90/10 to 99/1.

Particles A for the Core

The mean size of particles A constituting the core of the composite particles preferably ranges from 0.001 to 1000 µm, more preferentially from 0.05 to 500 µm, more particularly from 0.1 to 200 µm, even more particularly from 1 to 10 µm and even more particularly from 0.1 to 1 µm.

The term "mean particle size" means the mean size of 50% by volume of the particles (D[0,5]) measured at 25° C. using a laser diffraction granulometer (e.g. Mastersizer 2000 from the company Malvern).

According to a particular form of the invention, the mean size of 90% by volume of the particles (D[0,9]), obtained at 25° C. using a laser diffraction granulometer (e.g. Mastersizer 2000 from the company Malvern) may range from 2 to 7 µm, preferably from 2 to 6 µm and more preferentially from 2 to 5 µm.

The particles of core A in accordance with the invention may be spherical or non-spherical. According to a particular form of the invention, the ratio of the largest dimension to the smallest dimension may range from 1 to 2.5, more preferentially from 1 to 2 and even more particularly from 1 to 1.5.

Among the materials constituting the particles A of the core of the composite particles of the invention, mention may be made of:

(i) crosslinked or non-crosslinked poly(meth)acrylate and polyalkyl (meth)acrylate polymers, especially polymethyl methacrylates, for instance the products sold under the trade names MR-7GC® by the company Soken, and the products SSX-101® and SSX-102® sold by the company Sekisui Plastics;
(ii) crosslinked organopolysiloxane elastomers such as those described in patents EP 242 219, EP 285 886 and EP 765 656 and in patent application JP-A-61-194 009.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has a limited ability to extend and to contract. This material is capable of regaining its original shape after stretching.

Thus, the organopolysiloxane elastomer can be obtained by a crosslinking addition reaction of diorganopolysiloxane containing at least one hydrogen bonded to silicon and of diorganopolysiloxane having ethylenically unsaturated groups bonded to silicon, in particular in the presence of a platinum catalyst; or by a dehydrogenation crosslinking condensation reaction between a diorganopolysiloxane comprising hydroxyl end groups and a diorganopolysiloxane containing at least one hydrogen bonded to silicon, in particular in the presence of an organotin compound; or by a crosslinking condensation reaction of a diorganopolysiloxane comprising hydroxyl end groups and of a hydrolyzable organopolysilane; or by thermal crosslinking of organopolysiloxane, in particular in the presence of an organic peroxide catalyst; or by crosslinking of organopolysiloxane via high-energy radiation, such as gamma rays, ultraviolet rays or an electron beam.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name) or Dimethicone Crosspolymer-3 (INCI name).

Mention may be made especially of the powders sold under the names Dow Corning 9505 Powder and Dow Corning 9506 Powder by the company Dow Corning, these powders having the INCI name: Dimethicone/vinyl Dimethicone Crosspolymer.

The organopolysiloxane powder may also be coated with silsesquioxane resin, as described, for example, in patent U.S. Pat. No. 5,538,793. Such elastomeric powders are sold under the names KSP-100, KSP-101, KSP-102, KSP-103, KSP-104 and KSP-105 by the company Shin-Etsu, and have the INCI name: Vinyl Dimethicone/Methicone Silsesquioxane Crosspolymer. As examples of organopolysiloxane powders coated with silsesquioxane resin that may advantageously be used according to the invention, mention may especially be made of the organopolysiloxane elastomers having the INCI name Vinyl Dimethicone/Methicone Silsesquioxane Crosspolymer, such as those sold under the commercial reference KSP-100 from the company Shin-Etsu.
(iii) polysaccharides, in particular natural polysaccharides or polysaccharides of natural origin.

Among the polysaccharides that may be used according to the invention, mention may be made of native or modified starches.

Native Starches

The starches that may be used in the present invention are more particularly macromolecules in the form of polymers consisting of elementary moieties which are anhydroglucose units (dextrose), linked via $\alpha(1,4)$ bonds of chemical formula $(C_6H_{10}O_5)_n$. The number of these moieties and their assembly make it possible to distinguish amylose, a molecule formed from about 600 to 1000 linearly linked glucose units, and amylopectin, a polymer branched approximately every 25 glucose residues ($\alpha(1,6)$ bond). The total chain may include between 10 000 and 100 000 glucose residues. Starch is described in particular in the *Kirk-Othmer Encyclopedia of Chemical Technology*, 3rd edition, volume 21, pages 492-507, Wiley Interscience, 1983. The relative proportions of amylose and amylopectin and their degree of polymerization vary as a function of the botanical origin of the starches. On average, a sample of native starch consists of about 25% amylose and 75% amylopectin. Occasionally, phytoglycogen is present (between 0% and 20% of the starch), which is an analog of amylopectin but branched every 10 to 15 glucose residues.

Starch may be in the form of semicrystalline granules: amylopectin is organized in leaflets, amylose forms a less well organized amorphous zone between the various leaflets. Amylose is organized in a straight helix with six glucoses per turn. It dissociates into assimilable glucose under the action of enzymes, amylases, all the more easily when it is in amylopectin form. Specifically, the helical formation does not promote the accessibility of starch to the enzymes. Starches are generally in the form of a white powder, which is insoluble in cold water, whose elemental particle size ranges from 3 to 100 microns. By treating it with hot water, starch paste is obtained. It is exploited in industry for its thickening and gelling properties.

The botanical origin of the starch molecules used in the present invention may be cereals or tubers. Thus, the starches are chosen, for example, from corn starch, rice starch, cassava starch, tapioca starch, barley starch, potato starch, wheat starch, sorghum starch and pea starch. The native starches are represented, for example, by the products sold under the names C*Amilogel™, Cargill Gel™, C* Gel™, Cargill Gum™, DryGel™ and C*Pharm Gel™ by the company Cargill, under the name Corn Starch by the company Roquette, and under the name Tapioca Pure by the company National Starch.

Modified Starches

The modified starches used in the composition of the invention may be modified via one or more of the following reactions: pregelatinization, degradation (acid hydrolysis, oxidation, dextrinization), substitution (esterification, etherification), crosslinking (esterification), bleaching.

More particularly, these reactions may be performed in the following manner:
pregelatinization by splitting the starch granules (for example drying and cooking in a drying drum);
acid hydrolysis giving rise to very rapid retrogradation on cooling;
oxidation with strong oxidizing agents (alkaline medium, in the presence of sodium hypochlorite NaOCl for example) leading to the depolymerization of the starch molecule and to the introduction of carboxyl groups into the starch molecule (mainly oxidation of the hydroxyl group at C6);
dextrinization in acid medium at high temperature (hydrolysis followed by repolymerization);
crosslinking with functional agents capable of reacting with the hydroxyl groups of the starch molecules, which will thus bond together (for example with glyceryl and/or phosphate groups);

esterification in alkaline medium for the grafting of functional groups, in particular C1-C6 acyl (acetyl), C1-C6 hydroxyalkyl (hydroxyethyl or hydroxypropyl), carboxymethyl or octenylsuccinic.

Monostarch phosphates (of the type St-O—PO-(OX)2), distarch phosphates (of the type St-O—PO-(OX)-O-St) or even tristarch phosphates (of the type St-O—PO—(O-St)$_2$) or mixtures thereof may especially be obtained by cross-linking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds can, for example, be sodium tripolyphosphate, sodium orthophosphate, phosphorus oxychloride or sodium trimetaphosphate.

The starch molecules may be derived from any plant source of starch, especially such as corn, potato, oat, rice, tapioca, sorghum, barley or wheat. It is also possible to use the hydrolyzates of the starches mentioned above.

The modified starches are represented, for example, by the products sold under the names C*Tex-Instant (pregelatinized adipate), C*StabiTex-Instant (pregelatinized phosphate), C*PolarTex-Instant (pregelatinized hydroxypropyl), C*Set (acid hydrolysis, oxidation), C*size (oxidation), C*BatterCrisp (oxidation), C*DrySet (dextrinization), C*Tex™ (acetyl distarch adipate), C*PolarTex™ (hydroxypropyl distarch phosphate), C* StabiTex™ (distarch phosphate, acetyl distarch phosphate) by the company Cargill, by distarch phosphates or compounds rich in distarch phosphate such as the product sold under the references Prejel VA-70-T AGGL (gelatinized hydroxypropyl cassava distarch phosphate) or Prejel TK1 (gelatinized cassava distarch phosphate) or Prejel 200 (gelatinized acetyl cassava distarch phosphate) by the company Avebe or Structure Zea from National Starch (gelatinized corn distarch phosphate). As examples of oxidized starches, use will be made especially of those sold under the name C*size from the company Cargill.

According to a particular form of the invention, the core particles A will be chosen from polysaccharides having:
  a wet point for oil of at least 25 ml/100 g, preferably ranging from 35 to 600 ml/100 g and more preferentially from 40 to 500 ml/100 g and
  a wet point for water of at least 50 mg/100 g, preferably from 100 to 600 ml/100 g and more preferentially from 40 to 500 ml/100 g.

The term "wet point for oil" means the amount of oil required to render the particles completely impregnated with the oil, which may be manifested by the formation of a paste with the test particles. It may be determined according to the following protocol:
  2 g of said particles are spread out with a spatula on a glass plate, while adding an oil such as an ester oil, for instance isononyl isononanoate with a viscosity at 25° C. of 9 centipoises and a density at 25° C. of 0.853 g/ml;
  when the particles become completely impregnated and begin to form a paste, the weight of the oil added is determined as the wet point for oil;

the wet point for oil is calculated from the equation:

Wet point (ml/100 g)={(weight of oil added)/2 g}×100/oil density.

Similarly, the term "wet point for water" means the amount of oil required to render the particle completely impregnated with the oil, which may be manifested by the formation of a paste with the test powder. It may be determined according to the following protocol:
  2 g of the particles are spread out with a spatula on a glass plate, while adding water with a density of 0.998 g/ml;
  when the particles become completely impregnated and begin to form a paste, the weight of water added is determined as the wet point for water;

the wet point for water is calculated from the equation:

Wet point (ml/100 g)={(weight of water added)/2 g}×100/water density.

It is preferable for the ratio of the wet point for water/wet point for oil of the polysaccharide particles constituting the core of the composite particles to be less than or equal to 5, more preferentially less than or equal to 4, even more preferentially less than or equal to 3 and even more particularly less than 2.

Celluloses and derivatives thereof may be used among the polysaccharides and, preferentially, said celluloses will be porous.

The porosity of celluloses may be determined by their specific surface area ranging from 0.05 m$^2$/g to 1500 m$^2$/g, more preferentially from 0.1 m$^2$/g to 1000 m$^2$/g and even more preferentially from 0.2 m$^2$/g to 500 m$^2$/g according to the BET method.

According to a particular form of the invention, cellulose may be of the I type or of the II type or any equivalent. Celluloses of II type will preferentially be used.

According to a particular form of the invention, the cellulose particles will be spherical.

The cellulose particles, which are preferably spherical, may be prepared, for example, according to the following process
(1) A calcium carbonate slurry, as aggregation inhibitor, is added to an alkaline solution of water-soluble anionic polymer and mixed with stirring.
(2) Viscose and the aqueous solution thus obtained in step (1) are mixed to form a dispersion of fine viscose particles.
(3) The dispersion of fine viscose particles obtained in step (2) is heated to aggregate in the dispersion, and then neutralized with an acid to form cellulose particles.
(4) The fine cellulose particles are separated from the stock solution obtained in step (3), and then washed and dried, if necessary.

Viscose is cellulose raw material. A viscose having a gamma of from 30% to 100% by weight and an alkaline concentration of from 4% to 10% by weight is preferably used. A water-soluble anionic polymer that may be used is a sodium salt of poly(acrylic acid) or a sodium salt of polystyrenesulfonic acid. Calcium carbonate is used to prevent the formation of aggregates of the viscose particles in the dispersion and to reduce the size of the cellulose particles. A calcium carbonate slurry that may be mentioned is the product Tama Pearl TP-221 GS® sold by Okutama Kogyo Co., Ltd. in Japan.

According to a particular form of the invention, the cellulose derivatives may be chosen from cellulose esters and cellulose ethers.

The term "cellulose ester" means a polymer formed from α(1-4) sequences of partially or totally esterified anhydroglucose rings, the esterification being obtained by reaction of one or all of the free hydroxyl functions of said anhydroglucose rings with a linear or branched carboxylic acid or a carboxylic acid derivative (acid chloride or acid anhydride) containing from 1 to 4 carbon atoms.

Preferably, the cellulose esters result from the reaction of a few free hydroxyl functions of said rings with a carboxylic acid containing from 1 to 4 carbon atoms.

Advantageously, the cellulose esters are chosen from cellulose acetates, cellulose propionates, cellulose butyrates, cellulose isobutyrates, cellulose acetobutyrates and cellulose acetopropionates, and mixtures thereof.

These cellulose esters may have a weight-average molecular weight ranging from 3000 to 1 000 000, preferably from 10 000 to 500 000 and more preferentially from 15 000 to 300 000.

The term "cellulose ether" means a polymer formed from α(1-4) sequences of partially or totally etherified anhydroglucose rings, some of the hydroxyl functions of said rings being substituted with a radical —OR, in which R is preferably a linear or branched alkyl radical containing from 1 to 4 carbon atoms.

The cellulose ethers are preferably chosen from cellulose alkyl ethers with a C1-C4 alkyl group such as cellulose methyl ether, cellulose propyl ether, cellulose isopropyl ether, cellulose butyl ether and cellulose isobutyl ether.

These cellulose ethers may have a weight-average molecular weight ranging from 3000 to 1 000 000, preferably from 10 000 to 500 000 and more preferentially from 15 000 to 300 000.

As core particles A chosen from spherical cellulose particles, mention may be made of the following commercial products sold by the company Daito Kasei in Japan:

Cellulobeads USF® (wet point for oil of 296.0 ml/100 g, wet point 400.8 ml/100 g, wet point for water/wet point for oil ratio 1.4) with a particle size of 4 µm (porous cellulose), Cellulobeads D-5® (wet point for oil of 49.8 ml/100 g, wet point 205 ml/100 g, wet point for water/wet point for oil ratio 4.1) with a particle size of 10 µm, Cellulobeads D-10® (wet point for oil of 44 ml/100 g, wet point 164 ml/100 g, wet point for water/wet point for oil ratio 4.1) with a particle size of 15 µm, Moiscell PW D-5 XP® (wet point for oil of 58.6 ml/100 g, wet point 281.5 ml/100 g, wet point for water/wet point for oil ratio 4.8) with a particle size of 10 µm (potassium succinate cellulose), Moiscell PW D-50 XP® (wet point for oil of 39.9 ml/100 g, wet point 160 ml/100 g, wet point for water/wet point for oil ratio 4) with a particle size of 50 µm (potassium succinate cellulose).

The products Cellulobeads USF® and Cellulobeads D-5® are preferential and more particularly the product Cellulobeads USF®.

(iv) polyamide particles.

The polyamide particles used in the invention may be those sold under the name Orgasol by the company Atochem. The process for obtaining these particles is the one described, for example, in document FR 2 619 385 or in document EP 303 530. These polyamide particles are moreover known according to their various physicochemical properties under the name polyamide 12 (INCI name: Nylon-12) or polyamide 6 (INCI name: Nylon-6). The particles used in the invention may also be those sold under the name SP500® by the company Kobo.

(v) particles of copolymer of styrene and of (meth)acrylic acid or a $(C_1-C_{20})$alkyl ester thereof under the INCI name: Styrene/Acrylates Copolymer, for instance the product sold under the trade name Sunspheres Powder® by the company Röhm & Haas, such as those described in patent U.S. Pat. No. 5,663,213 and patent application EP 1 092 421.

(vi) polymethylsilsesquioxanes which are obtained by hydrolysis and condensation of methyltrimethoxysilane such as the products sold under the trade names AEC Silicone Resin Spheres® (A & E Connock (Perfumery & Cosmetics) Ltd.), Belsil PMS MK® (Wacker Chemie AG), Granpowder BU19® (Grant Industries, Inc.), Gransil PSQ® (Grant Industries, Inc.), Gransil PSQ-W® (Grant Industries, Inc.), KMP-590® (Shin-Etsu Chemical Co.), KMP-599® (Shin-Etsu Chemical Co.), MSP-K050® (Nikko Rica Corporation), SilDerm SQ® (Active Concepts LLC), SilForm Flexible Resin® (Momentive Performance Materials), Sil-Pearl 508® (Koda Corporation), Si-Tec PMS® (Ashland Inc.), Tospearl 2000®, Tospearl 120A®, Tospearl 130A®, Tospearl 145A®, Tospearl 1110A®, Tospearl 3000A®, Tospearl 2000B® and Tospearl 150KA® (Momentive Performance Materials).

(vii) inorganic particles;

Among the inorganic particles, examples that may be mentioned include:
metal oxides such as zirconium oxides, cerium oxides, iron oxides and titanium oxides,
alumina,
silicates such as talc, clays and kaolin,
glass particles,
silica (silicon dioxide),
calcium carbonate or magnesium carbonate,
magnesium hydrogen carbonates,
hydroxyapatite.

Among the silica particles, mention may be made of hollow spherical silica particles such as the products sold under the trade names Silica Beads SB 700® and Silica Beads SB 700 from the company Maprecos, and Sunspheres H-33® and Sunspheres H-51® from the company Asahi Glass.

(vii) mixtures thereof.

According to a particular form of the invention, the core particles B will be chosen from hydrophilic organic or inorganic particles.

Particles B for the Envelope

The mean size of the particles constituting the envelope of the composite particles of the invention may be from at least 0.01 to 100 µm, more preferentially from 0.05 to 50 µm and more particularly from 0.1 to 1 µm.

The term "mean particle size" means the mean size of 50% by volume of the particles (D[0,5]) measured at 25° C. using a laser diffraction granulometer (e.g. Mastersizer 2000 from the company Malvern).

The particles B in accordance with the invention may be spherical or non-spherical. According to a particular form of the invention, the ratio of the largest dimension to the smallest dimension may range from 1 to 2.5, more preferentially from 1 to 2 and even more particularly from 1 to 1.5.

Among the materials constituting the envelope of the composite particles in accordance with the invention, mention may be made of:
(i) polymethylsilsesquioxanes such as those mentioned previously;
(ii) crosslinked or non-crosslinked poly(meth)acrylate polymers such as those mentioned previously;
(iii) fumed silicas.

The fumed silicas may be hydrophilic or lipophilic.

The hydrophilic fumed silicas are obtained by pyrolysis of silicon tetrachloride (SiCl4) in a continuous flame at 1000° C. in the presence of hydrogen and oxygen. Among the fumed silicas of hydrophilic nature that may be used according to the present invention, mention may especially be made of those sold by the company Degussa or Evonik Degussa under the trade names Aerosil® 90, 130, 150, 200, 300 and 380 or alternatively by the company Cabot under the name Carbosil H5.

The lipophilic fumed silicas may be hydrophobic-surface-treated fumed silicas. This is because it is possible to chemically modify the surface of the silica, by chemical reaction generating a reduction in the number of silanol groups present at the surface of the silica. It is especially possible to substitute silanol groups with hydrophobic groups: a hydrophobic silica is then obtained.

The hydrophobic groups may be:
trimethylsiloxyl groups, which are obtained especially by treating fumed silica in the presence of hexamethyldisilazane. Silicas thus treated are known as "silica silylate" according to the CTFA (8th Edition, 2000). They are sold, for example, under the references Aerosil R812® by the company Degussa, and Cab-O-Sil TS-530® by the company Cabot;
dimethylsilyloxyl or polydimethylsiloxane groups, which are especially obtained by treating fumed silica in the presence of polydimethylsiloxane or dimethyldichlorosilane. Silicas thus treated are known as "Silica Dimethyl Silylate" according to the CTFA (8th Edition, 2000). They are sold, for example, under the references Aerosil R972® and Aerosil R974® by the company Degussa, and Cab-O-Sil TS-610® and Cab-O-Sil TS-720® by the company Cabot.

(iv) hydroxyapatites (Calcium Phosphate Hydroxide) such as the commercial products sold under the names Apatite Powder AD-10 (Advance Company, Ltd.), Hydroxysomes® (Laboratory Skin Care (LSC), Inc.) and Pearl Apatite® (Mikimoto Pharmaceutical Co., Ltd.).

(v) coated or uncoated metal oxide particles.

They may be chosen especially from titanium oxide, zinc oxide, iron oxide, zirconium oxide and cerium oxide, or mixtures thereof. According to the invention, coated or uncoated titanium oxide particles are particularly preferred.

Such coated or uncoated metal oxide particles are described in particular in patent application EP-A-0 518 773. Commercial pigments that may be mentioned include the products sold by the companies Sachtleben Pigments, Tayca, Merck and Degussa.

The metal oxide particles may be coated or uncoated. They have a mean elementary particle size of less than or equal to 0.5 μm, more preferentially between 0.005 and 0.5 μm, even more preferentially between 0.01 and 0.2 μm, better still between 0.01 and 0.1 μm and more particularly between 0.015 and 0.05 μm.

The coated particles are particles that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.

The coated particles are more particularly titanium oxides that have been coated:
with silica, such as the product Sunveil® from the company Ikeda,
with silica and iron oxide, such as the product Sunveil F® from the company Ikeda,
with silica and alumina, such as the products Microtitanium Dioxide MT 500 SA® and Microtitanium Dioxide MT 100 SA from the company Tayca and Tioveil from the company Tioxide,
with alumina, such as the products Tipaque TTO-55 (B)® and Tipaque TTO-55 (A)® from the company Ishihara and UVT 14/4 from the company Sachtleben Pigments,
with alumina and aluminum stearate, such as the products Microtitanium Dioxide MT 100 T®, MT 100 TX®, MT 100 Z® and MT-01® from the company Tayca, the products Solaveil CT-10 W® and Solaveil CT 100® from the company Uniqema and the product Eusolex T-AVO® from the company Merck,
with silica, alumina and alginic acid, such as the product MT-100 AQ® from the company Tayca,
with alumina and aluminum laurate, such as the product Microtitanium Dioxide MT 100 S® from the company Tayca,
with iron oxide and iron stearate, such as the product Microtitanium Dioxide MT 100 F® from the company Tayca,
with zinc oxide and zinc stearate, such as the product BR 351® from the company Tayca,
with silica and alumina and treated with a silicone, such as the products Microtitanium Dioxide MT 600 SAS®, Microtitanium Dioxide MT 500 SAS® or Microtitanium Dioxide MT 100 SAS® from the company Tayca,
with silica, alumina and aluminum stearate and treated with a silicone, such as the product STT-30-DS® from the company Titan Kogyo,
with silica and treated with a silicone, such as the product UV-Titan X 195® from the company Sachtleben Pigments,
with alumina and treated with a silicone, such as the products Tipaque TTO-55 (S)® from the company Ishihara or UV Titan M 262® from the company Sachtleben Pigments,
with triethanolamine, such as the product STT-65-S from the company Titan Kogyo,
with stearic acid, such as the product Tipaque TTO-55 (C)® from the company Ishihara,
with sodium hexametaphosphate, such as the product Microtitanium Dioxide MT 150 W® from the company Tayca,
$TiO_2$ treated with octyltrimethylsilane, sold under the trade name T 805® by the company Degussa Silices,
$TiO_2$ treated with a polydimethylsiloxane, sold under the trade name 70250 Cardre UF TiO2SI3® by the company Cardre,
anatase/rutile $TiO_2$ treated with a polydimethylhydrogenosiloxane, sold under the trade name Microtitanium Dioxide USP Grade Hydrophobic® by the company Color Techniques.

The uncoated titanium oxide particles are sold, for example, by the company Tayca under the trade names Microtitanium Dioxide MT 500 B or Microtitanium Dioxide MT 600 B®, by the company Degussa under the name P 25, by the company Wackher under the name Transparent titanium oxide PW®, by the company Miyoshi Kasei under the name UFTR®, by the company Tomen under the name ITS® and by the company Tioxide under the name Tioveil AQ®.

(vi) mixtures thereof.

Among the materials constituting the particles B, mention may also be made of poly-β-alanine powders, polyethylene powders; tetrafluoroethylene (Teflon®) powders, polyurea powders; polyurethane powders such as the copolymer of hexamethylene diisocyanate and of trimethylol sold under the name Plastic Powder D-400® by Toshiki; hollow expanded particles of vinylidene chloride and acrylonitrile polymer, such as the product sold under the name Expancel® by the company Expancel.

According to a particular form of the invention, the composite particles are chosen from:
composite particles whose core is formed from cross-linked polymethyl methacrylate and whose envelope is formed from hydroxyapatite, such as those sold under the name PAC-2® by the company Sekisui Plastics;
composite particles whose core is formed from cross-linked polymethyl methacrylate and whose envelope is formed from fumed silica, such as the product sold under the trade name Micropearl M330® by the company Matsumoto Yushi;
composite particles whose core is formed from organopolysiloxane elastomer and whose envelope is formed from fumed silica, such as the particles whose core is formed from Dimethicone/Vinyl Dimethicone Crosspolymer and whose envelope is formed from fumed silica, such as the product sold under the name DC 9701 Cosmetic Powder® by Dow Corning (INCI name: Dimethicone/Vinyl Dimethicone Crosspolymer (and) Silica);
composite particles whose core is formed from cross-linked polymethyl methacrylate and whose envelope is formed from polymethylsilsesquioxane, such as the product sold under the name Silcrusta MK03® from Kobo (INCI name: Methyl Methacrylate Crosspolymer (and) Polymethylsilsesquioxane);
composite particles whose core is formed from a polysaccharide, which is in particular natural or of natural origin, and whose envelope is formed from polymethyl methacrylate;
composite particles whose core is formed from polymethyl methacrylate and whose envelope is formed from fumed silica;
composite particles whose core is formed from polymethylsilsesquioxane and whose envelope is formed from fumed silica;
composite particles whose core is formed from polymethyl methacrylate and whose envelope is formed from titanium oxide; in particular titanium oxide coated with silica, alumina and alginic acid, such as the product MT-100 AQ from the company Tayca.

According to a particular form of the invention, the composite particles in accordance with the invention are composite particles whose core is formed from a polysaccharide, which is in particular natural or of natural origin, and whose envelope is formed from polymethyl methacrylate.

More preferentially, use will be made of a polysaccharide having:
a wet point for oil of at least 25 ml/100 g, preferably ranging from 35 to 600 ml/100 g and more preferentially from 40 to 500 ml/100 g and
a wet point for water of at least 50 mg/100 g, preferably from 100 to 600 ml/100 g and more preferentially from 40 to 500 ml/100 g.

Even more preferentially, use will be made of a polysaccharide whose ratio of the wet point for water/wet point for oil of the polysaccharide particles constituting the core of the composite particles is less than or equal to 5.0, more preferentially less than or equal to 4, even more preferentially less than or equal to 3.0 and even more particularly less than or equal to 2.0.

More particularly, use will be made of a porous cellulose, and better still a type II cellulose.

Preparation Process

The composite particles in accordance with the invention may be manufactured according to the standard techniques for manufacturing core/shell composite particles.

According to a preferential manufacturing method, the composite particles in accordance with the invention will be synthesized according to a dry coating technique (without liquid medium), in particular according to the mechanochemical melting technique.

A mechanochemical melting process consists of a process in which mechanical power such as a compression force, a friction force or shear is exerted on a plurality of elements, bringing about the melting of said elements.

The mechanochemical melting process may be performed with a machine comprising a rotary chamber and an internal part attached to a scraper, such as the machine sold under the trade name Hosokawa Micron Corporation, Japan.

A mechanochemical melting hybridizer process will preferably be used.

The hybridizer process was developed in the 1980s. The hybridizer process is a type of mechanochemical melting process in which strong mechanical power is applied to a plurality of particles in order to bring about a mechanochemical reaction so as to form composite particles.

According to the hybridizer process, the mechanical power is produced by a high-speed rotor which may have a diameter ranging from 10 cm to 1 m and which can rotate at a speed ranging from 1000 to 10 000 rpm. The hybridizer process may be performed in air or under a dry atmosphere. Specifically, high-speed rotation of the rotor can generate a flow of air at high speed in proximity to the rotor. Liquid materials may be subjected to the hybridizer process in the presence of solid materials.

The hybridizer process may be performed using a hybridization system sold under the trade name Nara Machinery, in which at least two types of particles, generally core particles and fine particles, are introduced into a hybridizer equipped with a high-speed rotor having a plurality of blades in a dry chamber, the particles are dispersed in the chamber and mechanical and thermal energy (compression, friction and shear) are exerted on the particles for a short period of time such as from 1 to 10 minutes and preferably from 1 to 5 minutes. As a result, particles of one type (fine particles) are integrated or fixed onto particles of another type (i.e. particles with a core) to form composite particles. It is preferable for the particles to be subjected to an electrostatic treatment, for example by shaking them to form an "ordered mixture" in which particles of one type are spread out to cover the other type of particles. The hybridizer process may be performed using a Theta composer sold by Tokuju Corporation.

The hybridizer process may be performed using a machine such as the Composi Hybrid or Mechano Hybrid machine sold by Nippon Coke.

Emulsions

The present invention relates to an emulsion not containing any emulsifying surfactant, comprising, especially in a physiologically acceptable medium, at least the particles as defined previously.

The emulsions in accordance with the invention are of the Pickering type, i.e. they are stabilized with fillers which are the composite particles as defined previously.

According to a particularly preferred form, the emulsions according to the invention are oil-in-water emulsions (or direct emulsion), i.e. they comprise a continuous aqueous phase and an oily phase dispersed in said aqueous phase in the form of oil droplets forming a mixture that is macroscopically homogeneous to the naked eye.

The mean size of the oil droplets, observed at room temperature (25° C.) using binocular magnifying glasses is preferably from 5 to 600 µm and more preferentially from 100 to 500 µm.

Preferentially, the composite particles of the invention will be present in the emulsions in concentrations ranging from 0.1% to 10% by weight and more preferentially from 0.5% to 2% by weight relative to the total weight of the composition.

The oil-in-water emulsions in accordance with the present invention may be prepared at room temperature (25° C.), via a preparation process comprising:
 a) dispersion of the composite particles in the aqueous phase, with stirring; and
 b) introduction of the oily phase into the aqueous phase with stirring; and
 c) optional addition of other ingredients; and
 d) mixing with stirring until the emulsion is formed and a macroscopically homogeneous mixture is obtained.

The invention thus relates to a process for preparing an oil-in-water emulsion free of emulsifying surfactant, as defined previously, comprising at least the following steps:
 a) dispersion, at room temperature (20-25° C.), of the composite particles in the aqueous phase, with stirring; and
 b) introduction of the oily phase into the aqueous phase with stirring; and
 c) optional addition of other ingredients; and
 d) mixing with stirring until the emulsion is formed and a macroscopically homogeneous mixture is obtained.

Aqueous Phase

The aqueous phase of a composition according to the invention comprises water and optionally a water-soluble solvent.

The water may especially be a floral water, a mineral water and/or a source water such as Vichy water, Lucas water or Roche Posay water.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the composition in a content ranging from 5% to 95%, better still from 30% to 80% by weight and preferably from 40% to 75% by weight relative to the total weight of said composition.

According to another embodiment variant, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols that are advantageously suitable for formulating a composition according to the present invention are those especially containing from 2 to 32 carbon atoms and preferably 3 to 16 carbon atoms.

Advantageously, the polyol may be chosen, for example, from ethylene glycol, pentaerythritol, trimethylolpropane, propylene glycol,
1,3-propanediol, butylene glycol, isoprene glycol, pentylene glycol, hexylene glycol, glycerol, polyglycerols such as glycerol oligomers, for instance diglycerol, and polyethylene glycols, and mixtures thereof.

According to a preferred embodiment of the invention, said polyol is chosen from ethylene glycol, pentaerythritol, trimethylolpropane, propylene glycol, glycerol, polyglycerols, polyethylene glycols and mixtures thereof.

According to a particular mode, the composition of the invention may comprise at least propylene glycol.

Oily Phase

For the purposes of the invention, the fatty phase includes any liquid fatty substance, generally oils (also known as liquid or oily fatty phase), or solid fatty substance like waxes or pasty compounds (also known as solid fatty phase).

In the sense of the invention, a liquid fatty phase is also called an oily phase and comprises at least one oil.

The term "oil" means any fatty substance that is in liquid form at room temperature and atmospheric pressure.

An oily phase that is suitable for preparing the cosmetic compositions according to the invention may comprise hydrocarbon-based oils, silicone oils, fluoro oils or nonfluoro oils, or mixtures thereof.

The oils may be volatile or nonvolatile.

They may be of animal, plant, mineral or synthetic origin. According to one implementation variant, oils of plant origin are preferred.

For the purposes of the present invention, the term "nonvolatile oil" means an oil with a vapor pressure of less than 0.13 Pa.

For the purposes of the present invention, the term "silicone oil" means an oil comprising at least one silicon atom, and in particular at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a nonzero vapor pressure, at room temperature and atmospheric pressure, especially having a vapor pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched $C_8$-$C_{16}$ alkanes, for instance $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, for instance isohexyl neopentanoate, and mixtures thereof. Preferably, the volatile hydrocarbon-based oil is selected from volatile hydrocarbon-based oils containing from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, mixtures of n-undecane ($C_{11}$) and of n-tridecane ($C_{13}$) obtained in Examples 1 and 2 of patent application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane and dodecamethylcyclohexasiloxane. Cyclohexasiloxane, Cyclopentasiloxane.

Nonvolatile Oils

The nonvolatile oils may be chosen especially from nonvolatile hydrocarbon-based, fluoro and/or silicone oils.

Nonvolatile hydrocarbon-based oils that may especially be mentioned include:
  linear or branched hydrocarbons of mineral or synthetic origin, such as petroleum jelly, polydecenes, hydrogenated polyisobutene such as Parleam®, squalane and liquid paraffins, and mixtures thereof,
  synthetic ethers containing from 10 to 40 carbon atoms, such as dicaprylyl ether,
  hydrocarbon-based oils of plant origin such as triglycerides consisting of fatty acid esters of glycerol, the fatty acids of which may have chain lengths varying from C4 to C24, these chains possibly being linear or branched, and saturated or unsaturated; these oils are especially heptanoic or octanoic acid triglycerides, or alternatively wheat germ oil, sunflower oil, grape seed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil and musk rose oil; or else caprylic/capric acid triglycerides, for instance those sold by the company Stéarineries Dubois or those sold under the names Miglyol 810®, 812® and 818® by the company Dynamit Nobel,
  synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \geq 10$. The esters may be chosen especially from alcohol fatty acid esters, for instance cetostearyl octanoate, isopropyl alcohol esters, such as isopropyl myristate, isopropyl palmitate, ethyl palmitate, 2-ethylhexyl palmitate, isopropyl stearate, octyl stearate, isocetyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, isononanoic acid esters, for instance isononyl isononanoate and isotridecyl isononanoate, and C12-C15 alkyl benzoates,
  polyol esters and pentaerythritol esters, for instance dipentaerythritol tetrahydroxystearate/tetraisostearate,
  non-phenyl silicone oils, for instance polydimethylsiloxanes, and
  phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicone with a viscosity of less than or equal to 100 cSt, and trimethylpentaphenyltrisiloxane, and mixtures thereof; and also mixtures of these various oils.

Another fatty substance that may be present in the oily phase may be, for example:
  a fatty acid chosen from fatty acids comprising from 8 to 30 carbon atoms, such as stearic acid, lauric acid, palmitic acid and oleic acid;
  a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;
  a gum chosen from silicone gums (dimethiconol);
  a pasty compound, such as polymeric or non-polymeric silicone compounds, esters of a glycerol oligomer, arachidyl propionate, fatty acid triglycerides and derivatives thereof;
  and mixtures thereof.

Preferably, a composition according to the invention comprises oils chosen from fatty alcohols, synthetic fatty acid esters and silicone oils, and mixtures thereof, more particularly chosen from isocetyl stearate, isopropyl myristate, C12-C15 alkyl benzoates, octyldodecanol, cyclohexasiloxane and polydimethylsiloxanes, and mixtures thereof.

A composition according to the invention may comprise from 5% to 95% by weight, better still from 5% to 40% by weight, and preferably from 7% to 35% by weight of oil(s) relative to the total weight of said composition.

Additives

The compositions according to the invention may, in addition, also comprise additional cosmetic and dermatological active agents.

The cosmetic compositions according to the invention may comprise cosmetic adjuvants chosen from softeners, antioxidants, opacifiers, stabilizers, moisturizers, vitamins, bactericides, preserving agents, sunscreens, polymers, fragrances, organic or mineral fillers, thickeners, gellants or suspension agents, or any other ingredient normally used in cosmetics for this type of application.

Thickeners that may be mentioned include carboxyvinyl polymers, such as Carbopols (Carbomers) and the Pemulens (acrylate/C10-C30 alkyl acrylate copolymer); polyacrylamides, for instance the crosslinked copolymers sold under the names Sepigel 305 (CTFA name: polyacrylamide/C13-C14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Clariant under the trade name Hostacerin AMPS (CTFA name: ammonium polyacryloyldimethyl taurate or Simulgel 800 sold by the company SEPPIC (CTFA name: sodium polyacryolyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethyl cellulose; polysaccharides and especially gums such as xanthan gum; and mixtures thereof.

The cosmetic compositions according to the invention may be used, for example, as makeup products for facial and/or bodily skin and/or the lips and/or the nails.

The cosmetic compositions according to the invention may be used, for example, as care, hygiene and/or sun protection products for facial and/or bodily skin and/or the lips and/or the nails, with a liquid to semi-liquid consistency, such as milks, creams of varying smoothness, cream gels or pastes.

They may optionally be packaged in aerosol form and may be in the form of a mousse or a spray.

The compositions according to the invention in the form of vaporizable fluid lotions in accordance with the invention are applied to the keratin materials in the form of fine particles by means of pressurizing devices.

The devices that are suitable for use in the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The terms "between . . . and . . . " and "ranging from . . . to . . . " should be understood as being inclusive of the limits, unless otherwise specified.

In the description and the examples, the percentages are percentages by weight. The ingredients are mixed in the order and under conditions that are easily determined by those skilled in the art.

EXAMPLES

Example 1: O/W Emulsion $E_T(30)A=44$ $E_T(30)B=55.2$ $\Delta E(30)=11.2$

| Phase A | |
| --- | --- |
| Particles of methyl methacrylate crosspolymer (and) hydroxyapatite (PAC-2 ®, Sekisui Plastics) | 1 g |
| Demineralized water | 66.5 g |
| Phase B | |
| Hydrogenated polyisobutene | 7 g |
| Cyclohexasiloxane | 6 g |
| Isocetyl stearate | 7 g |
| Phase C | |
| Xanthan gum | 0.5 g |
| Demineralized water | 10 g |
| Ethanol | 2 g |

1 g of PAC-2 particles was dispersed at room temperature (25° C.) in 66.6 g of demineralized water (phase A) using a paddle (Heidolph RZR2041), and phase B was then introduced slowly with continued stirring at 300 rpm for 1 hour. Phase C was then added with slow stirring. An oil-in-water emulsion that is stable after 24 hours at room temperature (25° C.), having oil drops with a mean diameter of 300 μm measured using binocular magnifying glasses, was obtained.

Example 2: O/W Emulsion $E_T(30)A=44$ $E_T(30)B=59.5$ $\Delta E(30)=15.5$

| Phase A | |
| --- | --- |
| Particles of methyl methacrylate crosspolymer (and) silica (Micropearl M330 ®, Matsumoto Yushi) | 1 g |
| Demineralized water | 66.5 g |
| Phase B | |
| Hydrogenated polyisobutene | 7 g |
| Cyclohexasiloxane | 6 g |
| Isocetyl stearate | 7 g |
| Phase C | |
| Xanthan gum | 0.5 g |
| Demineralized water | 10 g |
| Ethanol | 2 g |

According to the same protocol as example 1, an oil-in-water emulsion that is stable after 24 hours at room temperature (25° C.), having oil drops with a mean diameter of 500 μm, was obtained.

Example 3: O/W Emulsion $E_T(30)A=38$
$E_T(30)B=59.5$
$\Delta E(30)=21.5$

| Phase A | |
|---|---|
| Particles of vinyl dimethicone crosspolymer (and) silica (DC 9701 Cosmetic Powder, Dow Corning) | 1 g |
| Demineralized water | 42.2 g |
| Glycerol | 7 g |
| Propylene glycol | 2 g |
| Phase B | |
| Dimethicone (viscosity: 10 cSt) | 7 g |
| Dimethicone (viscosity: 5 cSt) | 4 g |
| Phase C | |
| Biosaccharide Gum-1 | 2 g |
| Demineralized water | 24.3 g |
| Polyacryldimethyltauramide | 0.5 g |
| Ethanol | 10 g |

According to the same protocol as example 1, an oil-in-water emulsion that is stable after 24 hours at room temperature (25° C.), having oil drops with a mean diameter of 100 μm, was obtained.

Example 4: O/W Emulsion $E_T(30)A=44$
$E_T(30)B=38$
$\Delta E(30)=6$

| Phase A | |
|---|---|
| Particles of methyl methacrylate crosspolymer (and) polymethylsilsesquioxane (Silcrusta MK03, Kobo) | 1 g |
| Demineralized water | 66.5 g |
| Phase B | |
| Dimethicone (viscosity: 10 cSt) | 20 g |
| Phase C | |
| Xanthan gum | 0.5 g |
| Demineralized water | 10 g |
| Ethanol | 2 g |

According to the same protocol as example 1, an oil-in-water emulsion that is stable after 24 hours at room temperature (25° C.), having oil drops with a mean diameter of 350 μm, was obtained.

Examples of Particles Obtained by Mechanofusion

| Example | Core | Envelope | ΔE(30) | Core/envelope weight ratio |
|---|---|---|---|---|
| MFP-1 | Cellulose (10 μm) (Cellulobeads D-5, Daito) | Acrylates Copolymer (0.35 μm) (MP-2200, Soken) | 7.4 | 97.5/2.5 |
| MFP-2 | Cellulose (10 μm) (Cellulobeads D-5, Daito) | Acrylates Copolymer (0.35 μm) (MP-2200, Soken) | 7.4 | 91.6/8.4 |
| MFP-3 | Methyl methacrylate crosspolymer (1.5 μm) (SSX-101, Sekisui Plastics) | Silica (Aerosil 200, Evonik) | 15.5 | 97.7/2.3 |
| MFP-4 | Methyl methacrylate crosspolymer (1.5 μm) (SSX-101, Sekisui Plastics) | Silica (Aerosil 200, Evonik) | 15.5 | 96.1/3.9 |
| MFP-5 | Methyl methacrylate crosspolymer (1.5 μm) (SSX-101, Sekisui Plastics) | Silica (Aerosil 200, Evonik) | 15.5 | 94.4/5.6 |
| MFP-6 | Polymethylsilsesquioxane (4.5 μm) (Tospearl 145A, Momentive) | Silica (Aerosil 200, Evonik) | 21.5 | 95.3/4.7 |
| MFP-7 | Methyl methacrylate crosspolymer (6 μm) (MR-7GC, Soken) | Silica (Aerosil 200, Evonik) | 15.5 | 98.9/1.1 |
| MFP-8 | Methyl methacrylate crosspolymer (2.5 μm) (SSX-102, Sekisui Plastics) | Titanium dioxide (MT-100AQ, Tayca) | 17.5 | 94.4/5.6 |

Procedure

For each example, the components indicated in the above table were mixed, in the weight ratio indicated in the same table, in a plastic bag which was shaken for a few minutes. The mixture was then placed in a hybridizer machine sold under the trade name Nara Machinery® with a rotor spinning at 8000 rpm (linear speed of 100 m/s) for 3 minutes to obtain the composite pigments.

Example 5: O/W Emulsion

| Phase A | |
|---|---|
| Composite particles MFP-1 | 1 g |
| Demineralized water | 66.5 g |
| Phase B | |
| Hydrogenated polyisobutene | 7 g |
| Cyclohexasiloxane | 6 g |
| Isocetyl stearate | 7 g |
| Phase C | |
| Xanthan gum | 0.5 g |
| Demineralized water | 12 g |

According to the protocol of example 1, an oil-in-water emulsion that is stable after 24 hours at room temperature (25° C.), having oil drops with a mean diameter of 300 μm, was obtained.

Example 6: O/W Emulsion

| Phase A | |
|---|---|
| Composite particles MFP-2 | 1 g |
| Demineralized water | 66.5 g |
| Phase B | |
| Dimethicone (10 cSt) | 20 g |
| Phase C | |
| Xanthan gum | 0.5 g |
| Demineralized water | 12 g |

According to the protocol of example 1, an oil-in-water emulsion that is stable after 24 hours at room temperature (25° C.), having oil drops with a mean diameter of 500 μm, was obtained.

Example 7: O/W Emulsion

| Phase A | |
|---|---|
| Composite particles MFP-3 | 1 g |
| Demineralized water | 66.5 g |
| Phase B | |
| Isopropyl myristate | 20 g |
| Phase C | |
| Xanthan gum | 0.5 g |
| Demineralized water | 12 g |

According to the protocol of example 1, an oil-in-water emulsion that is stable after 24 hours at room temperature (25° C.), having oil drops with a mean diameter of 260 μm, was obtained.

Example 8: O/W Emulsion

| Phase A | |
|---|---|
| Composite particles MFP-4 | 1 g |
| Demineralized water | 66.5 g |
| Phase B | |
| Hydrogenated polyisobutene | 20 g |
| Phase C | |
| Xanthan gum | 0.5 g |
| Demineralized water | 12 g |

According to the protocol of example 1, an oil-in-water emulsion that is stable after 24 hours at room temperature (25° C.), having oil drops with a mean diameter of 250 μm, was obtained.

Example 9: O/W Emulsion

| Phase A | |
|---|---|
| Composite particles MFP-5 | 1 g |
| Demineralized water | 66.5 g |
| Phase B | |
| Hydrogenated polyisobutene | 20 g |
| Phase C | |
| Xanthan gum | 0.5 g |
| Demineralized water | 12 g |

According to the protocol of example 1, an oil-in-water emulsion that is stable after 24 hours at room temperature (25° C.), having oil drops with a mean diameter of 250 μm, was obtained.

Examples 10 to 12: O/W Emulsions

TABLE 1

| | Example 10 (invention) | Example 11 (outside the invention) | Example 12 (outside the invention) |
|---|---|---|---|
| | Composite particles MFP-6 with a core made of Polymethylsilsesquioxane (Tospearl 145A ®) and an envelope made of fumed silica (Aerosil 200 ®) | Particles of fumed silica (Aerosil 200 ®) | Particles of Polymethylsilsesquioxane (4.5 μm) (Tospearl 145A ®) |

Common Support

| Phase A | |
|---|---|
| Particles according to table 1 | 0.5 g |
| Demineralized water | 39.5 g |
| Phase B | |
| Hydrogenated polyisobutene | 3.5 g |
| Cyclohexasiloxane | 3 g |
| Isocetyl stearate | 3.5 g |

0.5 g of particles in 39.5 g of demineralized water (phase A) was dispersed at room temperature (25° C.) by inversion in a test tube, and phase B was then introduced. Emulsification was performed by manual shaking for 30 seconds.

After 24 hours at room temperature (25° C.), it was found that only example 10 according to the invention prepared with the composite particles MFP-6 was stable, whereas emulsions 11 and 12 prepared with the core alone (Tospearl 145A) or the shell alone (Aerosil 200) were unstable (strong coalescence and two-phase system).

Example 13: O/W Emulsion

| Phase A | |
|---|---|
| Demineralized water | 39.5 g |
| Glycerol | 7 g |
| Propylene glycol | 2 g |
| Particles MFP-2 | 1 g |
| Phase B | |
| Dimethicone (10 cSt) | 7 g |
| Dimethicone (5 cSt) | 4 g |
| Phase C | |
| Biosaccharide Gum-1 | 2 g |
| Phase D | |
| Ammonium polyacryloyldimethyl taurate | 0.5 g |
| Demineralized water | 26.3 g |
| Phase E | |
| Phenoxyethanol | 0.7 g |
| Ethanol | 10 g |

1 g of MFP-2 particles was dispersed at room temperature (25° C.) in phase A using a paddle (Heidolph RZR2041) for 5 minutes at 300 rpm, and phase B was then introduced slowly with continued stirring at 300 rpm for 1 hour. Phase C was then added with gentle stirring, followed successively by phase D and E. An O/W emulsion that was stable after 24 hours at room temperature (25° C.), having oil drops with a mean diameter of 150 μm, was obtained.

Example 14: O/E Emulsion with Emulsifying Surfactant (Outside the Invention)

| Phase A | |
|---|---|
| Demineralized water | 38.8 g |
| Glycerol | 7 g |
| Propylene glycol | 2 g |
| Phase B | |
| Dimethicone (10 cSt) | 7 g |
| PEG-12 Dimethicone (emulsifying surfactant) | 0.7 g |
| Dimethicone (5 cSt) | 4 g |
| Phase C | |
| Biosaccharide Gum-1 | 2 g |
| Phase D | |
| Ammonium polyacryloyldimethyl taurate | 0.5 g |
| Demineralized water | 26.3 g |
| Phase E | |
| Phenoxyethanol | 0.7 g |
| Ethanol | 10 g |
| Phase F | |
| Particles MFP-2 | 1 g |

According to the protocol of example 16, an O/W emulsion that is stable after 24 hours at room temperature (25° C.), having oil drops with a mean diameter of 50 μm, was obtained.

Measurement of the Mattness/Gloss

Protocol for Measuring the Mattness of a Composition

The gloss of a deposit resulting from the application of a composition may be commonly measured according to various methods, such as the method using a Byk Micro TRI gloss 60° glossmeter.

Principle of the Measurement Using this Glossmeter

The machine illuminates the sample to be analyzed at a certain incidence and measures the intensity of the specular reflection.

The intensity of the reflected light depends on the material and on the angle of illumination. For non-ferrous materials (paint, plastic), the intensity of reflected light increases with the angle of illumination. The rest of the incident light penetrates the material and, depending on the shade of the color, is either partly absorbed or scattered.

The reflectometer measurement results are not based on the amount of incident light but on a polished black glass standard of defined refractive index.

The measurement is normalized relative to an internal standard and brought to a value out of 100: for this calibration standard, the measurement value is set at 100 gloss units (calibration).

The closer the measured value is to 100, the more glossy the sample. The measurement unit is the Gloss Unit (GU).

The angle of illumination used has a strong influence on the reflectometer value. In order to be able to readily differentiate very glossy and matt surfaces, the standardization has defined 3 geometries or 3 measurement domains.

Test Protocol a—Spread a coat with a wet thickness of 30 μm of the composition whose mean gloss value it is desired to evaluate onto an Erichsen Type 24/5® brand contrast card, using an automatic spreader. The coat covers the white background and the black background of the card.

b—Leave to dry for 24 hours at 37° C.

c—Measure the gloss at an angle of 60° on the matt white absorbent background (3 measurements) using a Byk Gardner brand glossmeter of reference microTri-Gloss.

| Composition | Gloss at 60° |
| --- | --- |
| Example 13 | GU = 10.5 ± 0.9 |
| Example 14 | GU = 20.8 ± 0.8 |

It was found that the composite particles had mattness properties that were maximized when they were used to stabilize the oil/water interface.

Example 15: O/W Emulsion

| Phase A | |
| --- | --- |
| Composite particles MFP-7 | 1 g |
| Demineralized water | 66.5 g |
| Phase B | |
| *Glycine Soya* Oil | 20 g |
| Phase C | |
| Xanthan gum | 0.5 g |
| Demineralized water | 12 g |

According to the same protocol as example 1, an O/W emulsion that is stable after 24 hours at room temperature (25° C.), having oil drops with a mean diameter of 50 μm, was obtained.

Example 16: O/W Emulsion

| Phase A | |
| --- | --- |
| Composite particles MFP-8 | 1 g |
| Demineralized water | 66.5 g |
| Phase B | |
| Isopropyl myristate | 20 g |
| Phase C | |
| Xanthan gum | 0.5 g |
| Demineralized water | 12 g |

According to the same protocol as example 1, an O/W emulsion that is stable after 24 hours at room temperature (25° C.), having oil drops with a mean diameter of 500 μm, was obtained.

The invention claimed is:

1. An emulsion comprising, in a physiologically acceptable medium, at least composite particles comprising:
   a core comprising at least organic or inorganic particles A;
   said core being covered, discontinuously, with an envelope comprising at least organic or inorganic particles B having a mean size of from 0.01 to 100 μm;
   said particles A and B having different polarities and being present in an emulsion stabilizing effective,
   wherein said emulsion is an oil-in-water emulsion comprising an oil phase dispersed in an aqueous phase, wherein said composite particles are dispersed in said aqueous phase, and wherein the oil-in-water emulsion does not comprise an emulsifying surfactant.

2. The emulsion according to claim 1, wherein the particles A and B have a difference in polarity $$\Delta E = E_T(30)A - E_T(30)B$$

of greater than 2.

3. The emulsion according to claim 1, wherein a weight ratio of the core to the envelope of the composite particles is from 70/30 to 99.9/0.1.

4. The emulsion according to claim 1, wherein the material constituting particles A of the core of the composite particles is selected from the group consisting of:
   (i) crosslinked or non-crosslinked poly(meth)acrylate polymers;
   (ii) crosslinked organopolysiloxane elastomers;
   (iii) polysaccharides that are natural or of natural origin;
   (iv) polyamide particles;
   (v) particles of copolymer of styrene and of (meth)acrylic acid or a (C1-C20)alkyl ester thereof;
   (vi) polymethylsilsesquioxanes;
   (vii) inorganic particles; and
   (viii) mixtures thereof.

5. The emulsion according to claim 1, wherein the material constituting particles B of the envelope of the composite particles is selected from the group consisting of:
   (i) polymethylsilsesquioxanes;
   (ii) crosslinked or non-crosslinked poly(meth)acrylate polymers;
   (iii) fumed silicas;
   (iv) hydroxyapatites;
   (v) coated or uncoated metal oxide particles;
   (vi) alumina; and
   (vii) mixtures thereof.

6. The emulsion according to claim 1, wherein the composite particles are selected from the group consisting of:
   composite particles whose core is formed from crosslinked polymethyl methacrylate and whose envelope is formed from hydroxyapatite;
   composite particles whose core is formed from crosslinked polymethyl methacrylate and whose envelope is formed from fumed silica;
   composite particles whose core is formed from organopolysiloxane elastomer and whose envelope is formed from fumed silica;
   composite particles whose core is formed from crosslinked polymethyl methacrylate and whose envelope is formed from polymethylsilsesquioxane;
   composite particles whose core is formed from a polysaccharide, and whose envelope is formed from polymethyl methacrylate;
   composite particles whose core is formed from polymethyl methacrylate and whose envelope is formed from fumed silica;
   composite particles whose core is formed from polymethylsilsesquioxane and whose envelope is formed from fumed silica; and
   composite particles whose core is formed from polymethyl methacrylate and whose envelope is formed from titanium oxide.

7. The emulsion according to claim 1, wherein the composite particles are composite particles whose core is formed from a polysaccharide, and whose envelope is formed from polymethyl methacrylate.

8. The emulsion according to claim 7, wherein the polysaccharide has:
   a wet point for oil of at least 25 ml/100 g, and
   a wet point for water of at least 50 mg/100 g, and a ratio of the wet point for water/wet point for oil of less than or equal to 5.

9. The emulsion according to claim 7, wherein the polysaccharide is a porous cellulose or a type II cellulose.

10. The emulsion according to claim 1, wherein the composite particles are obtained by chemical mechanofusion.

11. The emulsion according to claim 1, wherein the composite particles are present in concentrations ranging from 0.1% to 10% by weight relative to the total weight of the emulsion.

12. A process for preparing the emulsion according to claim 1, comprising:
   a) dispersion, at room temperature (20-25° C.), of the composite particles comprising a core comprising at least organic or inorganic particles A;
   said core being covered, discontinuously, with an envelope comprising at least organic or inorganic particles B;
   said particles A and B having different polarities, with stirring; and
   b) introduction of the oily phase into the aqueous phase with slow stirring; and
   c) optional addition of other ingredients; and
   d) mixing with stirring until the emulsion is formed and a macroscopically homogeneous mixture is obtained.

13. A cosmetic process for treating a keratin material, comprising:
   applying to the keratin material an emulsion according to claim 1.

14. The emulsion according to claim 1, wherein the materials A and B have a difference in polarity $$\Delta E = E_T(30)A - E_T(30)B$$

of greater than 5.

15. The emulsion according to claim 1, wherein the composite particles have a mean size ranging from 0.5 to 15 µm and a weight ratio of the core to the envelope of the composite particles is from 80/20 to 99/1.

16. The emulsion according to claim 1, wherein the composite particles have a mean size ranging from 1 to 10 µm and a weight ratio of the core to the envelope of the composite particles is from 90/10 to 99/1.

17. The emulsion according to claim 1, wherein 10% to 90% of the surface of the core is surrounded with an envelope comprising at least organic or inorganic particles B.

18. The emulsion according to claim 1, wherein the organic or inorganic particles B have a mean size of from 0.05 to 50 µm.

19. The emulsion according to claim 1, wherein particles A are organic.

* * * * *